US011465289B2

(12) United States Patent
Masaki et al.

(10) Patent No.: US 11,465,289 B2
(45) Date of Patent: Oct. 11, 2022

(54) APPARATUS AND METHOD FOR CONTROLLING CONTINUUM ROBOT, AND COMPUTER-READABLE STORAGE MEDIUM

(71) Applicant: CANON KABUSHIKI KAISHA, Tokyo (JP)

(72) Inventors: Fumitaro Masaki, Brookline, MA (US); Kiyoshi Takagi, Tokyo (JP); Yusuke Tanaka, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 51 days.

(21) Appl. No.: 16/924,805

(22) Filed: Jul. 9, 2020

(65) Prior Publication Data
US 2020/0338743 A1    Oct. 29, 2020

Related U.S. Application Data

(63) Continuation of application No. PCT/JP2018/047593, filed on Dec. 25, 2018.

(30) Foreign Application Priority Data

Jan. 12, 2018  (JP) .............................. JP2018-003724

(51) Int. Cl.
| | | |
|---|---|---|
| B25J 9/16 | (2006.01) | |
| B25J 9/10 | (2006.01) | |
| B25J 13/08 | (2006.01) | |

(52) U.S. Cl.
CPC ............. *B25J 9/1697* (2013.01); *B25J 9/104* (2013.01); *B25J 9/1664* (2013.01); *B25J 13/08* (2013.01)

(58) Field of Classification Search
CPC ........ B25J 9/1697; B25J 9/104; B25J 9/1664; B25J 13/08; B25J 19/021; B25J 18/06;
(Continued)

(56) References Cited

U.S. PATENT DOCUMENTS 9,566,711 B2 *  2/2017  Smith ............... G05B 19/41815
10,254,499 B1 *  4/2019  Cohen ....................... G02B 6/25
(Continued)

FOREIGN PATENT DOCUMENTS

| JP | 2004-248366 A | 9/2004 |
|---|---|---|
| JP | 2007-090098 A | 4/2007 |

(Continued)

OTHER PUBLICATIONS

Bajo, Andrea, et al., "Hybrid motion/force control of multi-backbone continuum robots", International Journal of Robotics Research, XP055812870, vol. 35, No. 4, Apr. 20, 2016 (Apr. 20, 2016), pp. 422-434, US ISSN: 0278-3649, DOi: 10.1177/0278364915584606.

(Continued)

*Primary Examiner* — Jaime Figueroa
(74) *Attorney, Agent, or Firm* — Canon U.S.A., Inc. I.P. Division

(57) ABSTRACT

A control apparatus for a continuum robot including a curved portion that is curved by driving a wire with a driving mechanism includes an image DB/torsional-amount acquisition unit that obtains the torsional amount of the continuum robot and a kinematic operation unit that sets the driving displacement amount of the wire driven by the driving mechanism on the basis of the torsional amount obtained by the image DB/torsional-amount acquisition unit.

19 Claims, 11 Drawing Sheets

(58) Field of Classification Search
CPC ...... A61B 2034/2065; A61B 2034/305; A61B 2034/306; A61B 2090/066; A61B 90/37; A61B 1/00154; G02B 23/24
USPC .................................................. 700/245–264
See application file for complete search history.

(56) References Cited

U.S. PATENT DOCUMENTS

| | | | |
|---|---|---|---|
| 10,543,605 B2* | 1/2020 | Piette | B25J 9/0018 |
| 10,571,642 B1* | 2/2020 | Cohen | H01R 4/024 |
| 10,743,750 B2* | 8/2020 | Hunter | A61B 1/0057 |
| 10,786,903 B2* | 9/2020 | Huang | G05D 1/0274 |
| 11,084,166 B2* | 8/2021 | Takagi | B25J 18/06 |
| 2012/0271109 A1 | 10/2012 | Belson | |
| 2013/0090763 A1* | 4/2013 | Simaan | A61B 5/11 700/258 |
| 2013/0300537 A1* | 11/2013 | Bajo | A61B 34/30 340/8.1 |
| 2014/0330432 A1* | 11/2014 | Simaan | A61B 34/35 700/250 |
| 2017/0182659 A1* | 6/2017 | Simaan | A61B 34/37 |
| 2018/0125593 A1* | 5/2018 | Sinibaldi | B25J 9/1085 |
| 2018/0304458 A1* | 10/2018 | Takagi | B25J 18/06 |
| 2019/0184553 A1* | 6/2019 | Takagi | B25J 9/163 |
| 2020/0375682 A1* | 12/2020 | Kincaid | A61B 34/76 |

FOREIGN PATENT DOCUMENTS

| | | |
|---|---|---|
| JP | 2007-159337 A | 6/2007 |
| JP | 2007-181267 A | 7/2007 |
| JP | 2007-306993 A | 11/2007 |
| JP | 2007-330348 A | 12/2007 |
| JP | 2008-048788 A | 3/2008 |
| JP | 2010-104426 A | 5/2010 |
| JP | 2015-530903 A | 10/2015 |
| WO | 2016/063682 A1 | 4/2016 |
| WO | 2017/014301 A1 | 1/2017 |
| WO | 2017/014308 A1 | 1/2017 |

OTHER PUBLICATIONS

Shi, Chaoyang, et al., "Shape Sensing Techniques for Continuum Robots in Minimally Invasive Surgery: A Survey", IEEE Transactions on Biomedical Engineering, IEEE Service Center, Piscataway, NJ, USA, XP011656270, vol. 64, No. 8, Aug. 1, 2017 (Aug. 1, 2017), pp. 1665-1678, ISSN: 0018-9294, DOI: 10.1109/TBME.2016.2622361.

Xu Kai et al, "An Exporimental Kinestatic Comparison betweenContinuum Manipulators with Structural Variations", IEEE International Conference on Robotics and Automatio4(ICRA), 2014, pp. 3258-3264.

* cited by examiner

APPARATUS AND METHOD FOR CONTROLLING CONTINUUM ROBOT, AND COMPUTER-READABLE STORAGE MEDIUM

CROSS-REFERENCE TO RELATED APPLICATIONS

This application is a Continuation of International Patent Application No. PCT/JP2018/047593, filed Dec. 25, 2018, which claims the benefit of Japanese Patent Application No. 2018-003724, filed Jan. 12, 2018, both of which are hereby incorporated by reference herein in their entirety.

BACKGROUND OF THE INVENTION

Field of the Invention

The present invention relates to a continuum-robot control apparatus, a method for controlling the same, and a computer-readable storage medium storing a program for causing a computer to function as the control apparatus.

Background Art

Continuum robots are also called continuum robots, which include a curved portion having a flexible structure and whose shape is controlled by deforming the curved portion. The continuum robots have mainly two advantages over rigid-link robots constituted by rigid links. First, continuum robots are movable along a curve in a narrow space in which a rigid-link robot would be caught or an environment in which scatters are present. Second, continuum robots have essential flexibility, and can be operated without damaging fragile objects. This does not necessarily need, for example, to detect an external force which is required by rigid-link robots.

Continuum robots are expected to be used in a medical field, for example, for sheaths and catheters of endoscopes, and ultimate working robots such as rescue robots. NPL 1 describes a technique of a continuum robot including a curved portion that is curved by driving wires. PTL 1 describes a control technique for making a continuum robot used as an endoscope intrude into a space. Specifically, PTL 1 describes a technique for controlling all of adjacent curved portion sets so that the curve of a curved portion in a forward section is formed into the curve shape of a curved portion in the following section as the base unit of the endoscope advances to thereby continuously propagate the curve shape.

CITATION LIST

Patent Literature

PTL 1: US2012/0271109

Non-Patent Literature

NPL 1: K. Xu, M. Fu, and J. Zhao, "An Experimental Kinestatic Comparison between Continuum Manipulators with Structural Variations," in IEEE International Conference on Robotics and Automation (ICRA), Hong Kong, China, 2014, pp. 3258-3264

When a continuum robot is inserted into an insertion-extraction path, such as a pipe or a body cavity, the continuum robot can come into contact with the inner wall of the insertion-extraction path to get twisted. When the continuum robot is twisted, for example, the correspondence relationship between the driving displacement amount of a wire for controlling the curved shape of the curved portion and the orientation of the continuum robot is deviated from the design value. This can decrease the accuracy of drive control of the continuum robot. NPL 1 and PTL 1 described above do not take into consideration of this point.

The present invention has been made in consideration of such a problem. It is therefore an object of the present invention to provide a mechanism for suppressing a decrease in the accuracy of drive control of a continuum robot even if the continuum robot is twisted.

SUMMARY OF THE INVENTION

A control apparatus for a continuum robot according to the present invention is a control apparatus for a continuum robot including a curved portion that is curved by driving a wire using a driving mechanism. The control apparatus includes an acquisition unit that obtains a torsional amount the continuum robot and a setting unit that sets a driving displacement amount of the wire driven by the driving mechanism based on the torsional amount obtained by the acquisition unit.

The present invention further includes a method for controlling a continuum robot using the continuum robot control apparatus described above, as well as a computer-readable storage medium storing a program for causing a computer to function as the continuum robot control apparatus.

Further features of the present invention will become apparent from the following description of exemplary embodiments with reference to the attached drawings.

DESCRIPTION OF THE EMBODIMENTS

Embodiments of the present invention will be described in detail hereinbelow with reference to the drawings. Embodiments of the present invention illustrate examples in which a control system for a continuum robot (also referred to as a continuum manipulator) is used for a flexible endoscope. The flexible endoscope used as an example of the continuum robot control system according to the embodiments of the present invention is used not only for a medical field but also for any other fields for observing the inside of a path in and out of which a curved portion is inserted and extracted (hereinafter referred to as "insertion-extraction path") (for example, industrial endoscopes for observing the inside of a pipe or the like).

First Embodiment

First, a first embodiment of the present invention will be described.

[1. Kinematic Model of Continuum Robot]

Figure 1:
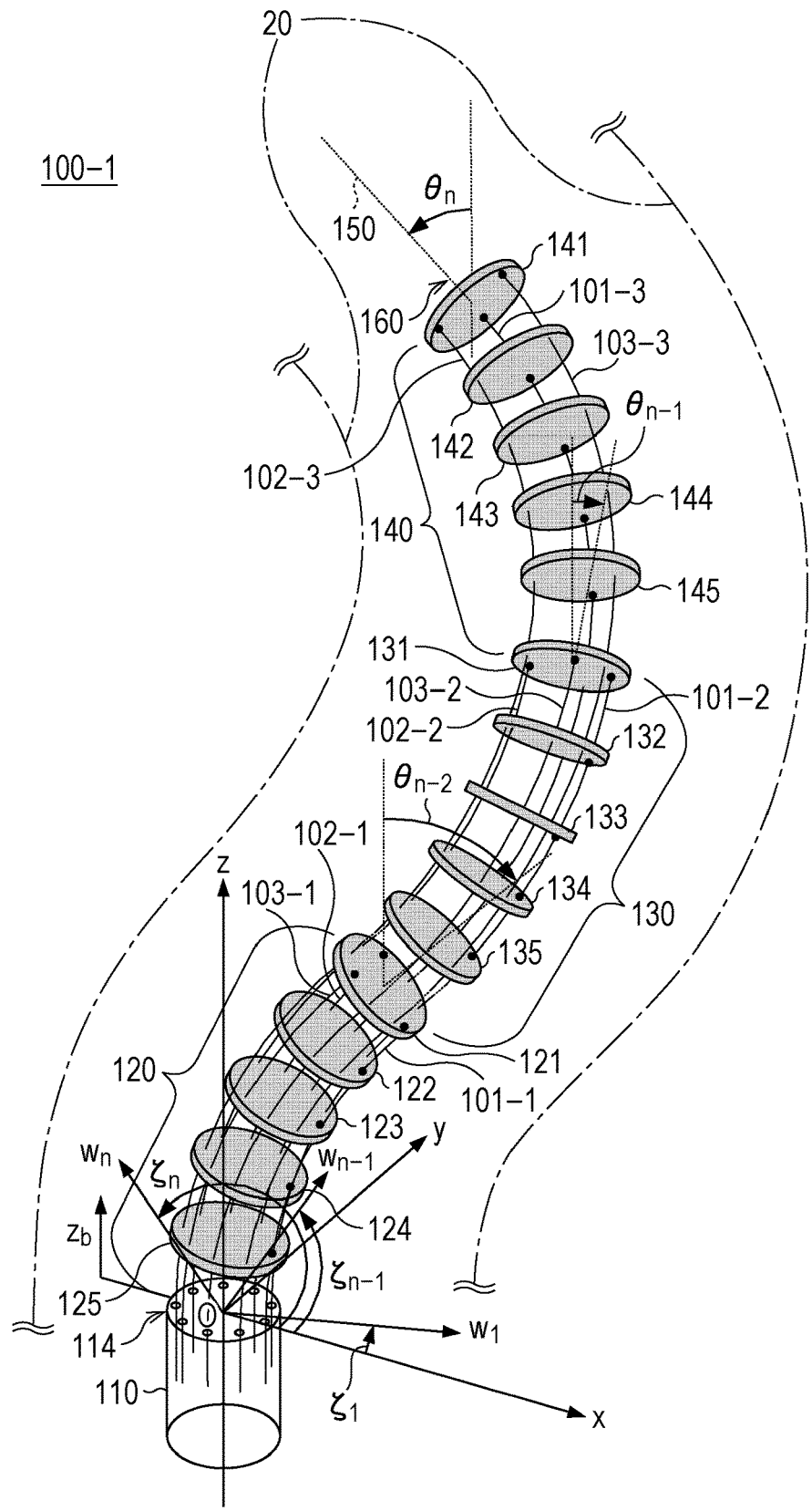
FIG. 1 is a diagram illustrating, in outline, an example of the configuration of a continuum robot according to a first embodiment of the present invention.

FIG. 1 is a diagram illustrating, in outline, an example of the configuration of a continuum robot 100-1 according to the first embodiment of the present invention.

As illustrated in FIG. 1, the continuum robot 100-1 includes a base unit 110 (FIG. 1 illustrates only a casing including an upper surface 114 of the base unit 110), a first curved portion 120, a second curved portion 130, and a third curved portion 140.

The continuum robot 100-1 illustrated in FIG. 1 includes a plurality of curved portions 120 to 140 in series in the direction of the long axis and is movable in the direction of the long axis of the plurality of curved portions 120 to 140. Although the example in FIG. 1 illustrates a continuum robot including three curved portions, the present embodiment is not limited to this configuration. For example, a continuum robot including two curved portions and a continuum robot including four or more curved portions can also be used in the present embodiment.

The first curved portion 120 includes a plurality of wires 101-1 to 103-1 extending through an upper surface 114 of the base unit 110 corresponding to the reference plane of the first curved portion 120, a first wire guide 121 in which the plurality of wires 101-1 to 103-1 are fixed at different positions and which guides the plurality of wires 101-1 to 103-1, and second wire guides 122 to 125 which are disposed between the upper surface 114 of the base unit 110 and the first wire guide 121, in which the predetermined wire 101-1 of the plurality of wires 101-1 to 103-1 is fixed at a predetermined position, and which guides the plurality of wires 101-1 to 103-1. As illustrated in FIG. 1, the plurality of wires 101-1 to 103-1 are not fixed to the upper surface 114 of the base unit 110.

The continuum robot 100-1 illustrated in FIG. 1 is configured such that the first curved portion 120 can be curved into a desired curved shape (for example, a circular arc) by driving at least part (or all) of the plurality of wires 101-1 to 103-1.

In the following description, in each of the components of the continuum robot 100-1, the end remote from the upper surface 114 of the base unit 110 is referred to as "distal end", and the end adjacent to the upper surface 114 of the base unit 110 is referred to as "proximal end". Specifically, the first curved portion 120 is from the upper surface 114 of the base unit 110 (strictly, the upper surface 114 itself is not included) to the distal end of the first wire guide 121. Here, for example, the wires 101-1 to 103-1 are fixed to different positions at the distal end of the first wire guide 121. For example, the wire 101-1 is fixed to the respective proximal ends of the second wire guides 122 to 125.

The second curved portion 130 includes a plurality of wires 101-2 to 103-2 extending through the distal surface of the first wire guide 121 of the first curved portion 120 corresponding to the reference plane of the second curved portion 130, a first wire guide 131 in which the plurality of wires 101-2 to 103-2 are fixed at different positions and which guides the plurality of wires 101-2 to 103-2, and second wire guides 132 to 135 which are disposed between the distal surface of the first wire guide 121 of the first curved portion 120 and the first wire guide 131, in which the predetermined wire 101-2 of the plurality of wires 101-2 to 103-2 is fixed to a predetermined position, and which guides the plurality of wires 101-2 to 103-2. As illustrated in FIG. 1, the plurality of wires 101-2 to 103-2 are not fixed to the upper surface 114 of the base unit 110.

The continuum robot 100-1 illustrated in FIG. 1 is configured such that the second curved portion 130 can be curved into a desired curved shape (for example, a circular arc) by driving at least part (or all) of the plurality of wires 101-2 to 103-2.

Specifically, the second curved portion 130 is from the distal surface of the first wire guide 121 of the first curved portion 120 (strictly, the distal surface itself is not included) to the distal end of the first wire guide 131. Here, for example, the wires 101-2 to 103-2 are fixed to different positions at the distal end of the first wire guide 131. F or example, the wire 101-2 is fixed to the respective proximal ends of the second wire guides 132 to 135.

The third curved portion 140 includes a plurality of wires 101-3 to 103-3 extending through the distal surface of the first wire guide 131 of the second curved portion 130 corresponding to the reference plane of the third curved portion 140, a first wire guide 141 in which the plurality of wires 101-3 to 103-3 are fixed at different positions and which guides the plurality of wires 101-3 to 103-3, and second wire guides 142 to 145 which are disposed between the distal surface of the first wire guide 131 of the second curved portion 130 and the first wire guide 141, in which the predetermined wire 101-3 of the plurality of wires 101-3 to 103-3 is fixed to a predetermined position, and which guides the plurality of wires 101-3 to 103-3. As illustrated in FIG. 1, the plurality of wires 101-3 to 103-3 are not fixed to the upper surface 114 of the base unit 110.

The continuum robot 100-1 illustrated in FIG. 1 is configured such that the third curved portion 140 can be curved into a desired curved shape (for example, a circular arc) by driving at least part (or all) of the plurality of wires 101-3 to 103-3.

Specifically, the third curved portion 140 is from the distal surface of the first wire guide 131 of the second curved portion 130 (strictly, the distal surface itself is not included) to the distal end of the first wire guide 141. Here, for example, the wires 101-3 to 103-3 are fixed to different positions at the distal end of the first wire guide 141. For example, the wire 101-3 is fixed to the respective proximal ends of the second wire guides 142 to 145.

FIG. 1 illustrates the center of the upper surface 114 of the base unit 110 as an origin O, as well as the x-axis and the y-axis passing through the origin O in the surface and perpendicular to each other. FIG. 1 also illustrates the z-axis perpendicular to the upper surface 114 of the base unit 110. FIG. 1 also illustrates the central axis 150 of the continuum robot 100-1 and a position 160 at which an imaging apparatus (an imaging apparatus 310 illustrated in FIGS. 5 and 6, for example) to be mounted to the continuum robot 100-1. Thus, mounting the imaging apparatus to the continuum robot 100-1 illustrated in FIG. 1 allows the inside of the insertion-extraction path 20 to be observed by inserting the continuum robot 100-1 along the insertion-extraction path 20. Although FIG. 1 illustrates an example in which a plurality of wire guides arranged discretely are disposed, a bellows or mesh continuum wire guide may be disposed.

Figure 2:
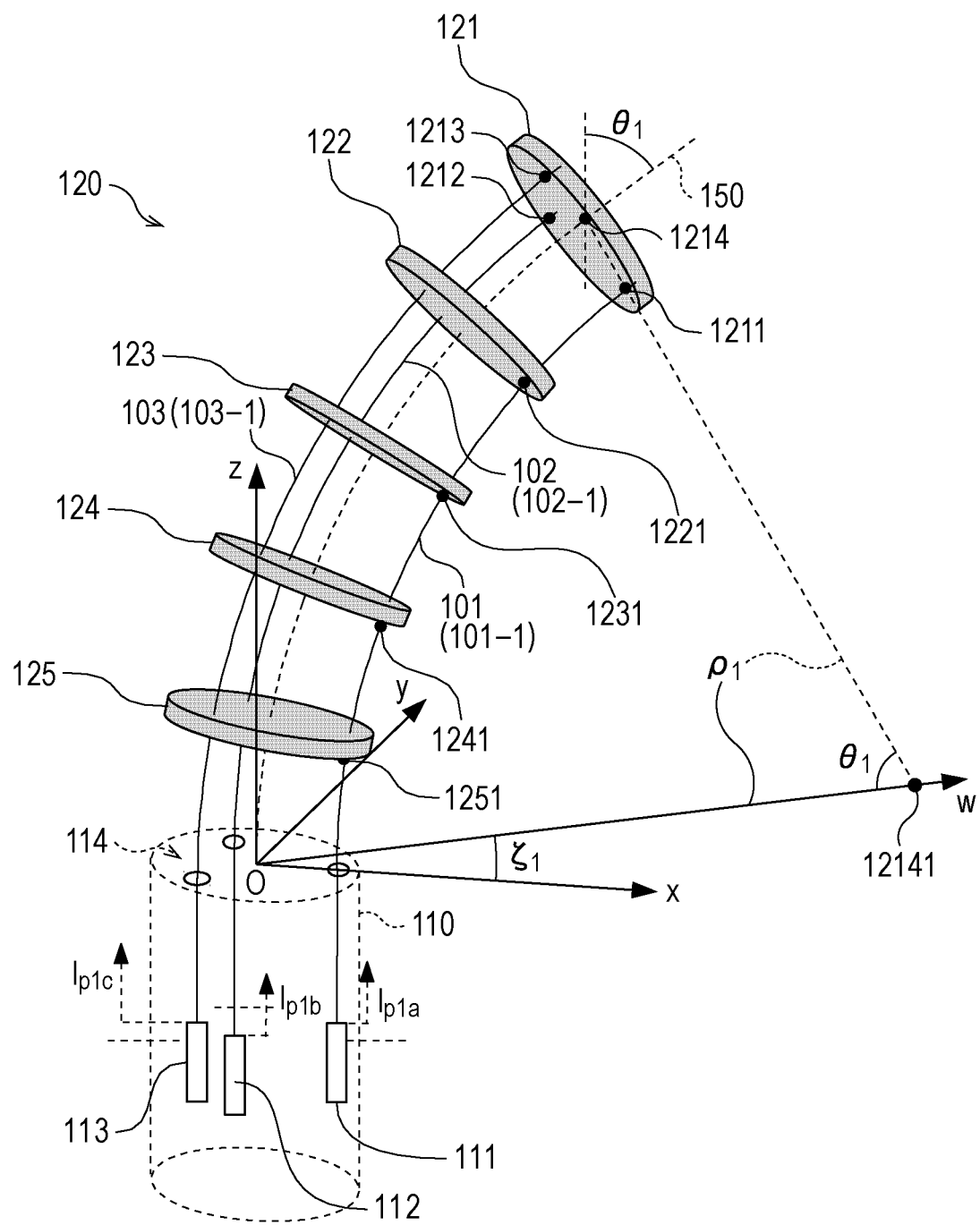
FIG. 2 is a schematic diagram of the first embodiment of the present invention, illustrating the details of a base unit and a first curved portion of the continuum robot illustrated in FIG. 1.

FIG. 2 is a schematic diagram of the first embodiment of the present invention, illustrating the details of the base unit 110 and the first curved portion 120 of the continuum robot 100-1 illustrated in FIG. 1. In FIG. 2, the same components as the components illustrated in FIG. 1 are given the same reference signs and detailed descriptions will be omitted.

Specifically, for the first wire guide 121 of the first curved portion 120 illustrated in FIG. 2, the wire 101-1 is fixed to a position 1211, the wire 102-1 is fixed to a position 1212, and the wire 103-1 is fixed to a position 1213. The positions 1211 to 1213 are different positions at the distal end of the first wire guide 121, as described above.

The second wire guide 122 is fitted with the wire 101-1 at a position 1221. The second wire guide 123 is fitted with the wire 101-1 at a position 1231. The second wire guide 124 is fitted with the wire 101-1 at a position 1241. The second wire guide 125 is fitted with the wire 101-1 at a position 1251. The positions 1221 to 1251 are respective proximal end positions of the second wire guides 122 to 125, as described above.

The base unit 110 has therein an actuator 111 for pushing and pulling the wire 101-1, an actuator 112 for pushing and pulling the wire 102-1, and an actuator 113 for pushing and pulling the wire 103-1. In other words, the continuum robot 100-1 illustrated in FIG. 1 is configured to curve the first curved portion 120 into a desired curved shape by controlling the actuators 111 to 113 to drive the wires 101-1 to 103-3, respectively. The orientation of the continuum robot 100-1 (the first curved portion 120) is controlled in this manner. The actuators 111 to 113 constitute a driving mechanism in the present invention.

In FIG. 2, the central axis 150 of the continuum robot 100-1 (more specifically, the first curved portion 120 in the example illustrated in FIG. 2) is indicated by the broken line, as in FIG. 1. FIG. 2 illustrates the x-axis, the y-axis, and the z-axis, as in FIG. 1. FIG. 2 illustrates the driving displacement amount $l_{p1a}$ of the wire 101-1 driven by the actuator 111, the driving displacement amount $l_{p1b}$ of the wire 102-1 driven by the actuator 112, and the driving displacement amount $l_{p1c}$ of the wire 103-1 driven by the actuator 113.

FIG. 2 also illustrates a position 1214 through which the central axis 150 passes at the distal end of the first wire guide 121. FIG. 2 also illustrates an angle formed by the central axis 150 and a line segment parallel to the z-axis at the position 1214 as the curve angle $\theta_1$ of the first curved portion 120. FIG. 2 also illustrates a w-axis, which is a projection of the central axis 150 on an x-y plane, and a position 12141, which is a projection of the position 1214 on the x-y plane. FIG. 2 also illustrates an angle formed by the x-axis and the w-axis as the rotational angle $\zeta_1$ of the first curved portion 120. FIG. 2 also illustrates the curvature radius $\rho_1$ of the first curved portion 120 about the central axis 150.

In the following description, the curved portion to be driven is generalized as the n-th curved portion (n is any positive number), and the following elements are defined for the n-th curved portion.

$l_n$: the length of the n-th curved portion (in the example of FIG. 2, the length of the central axis 150 from the origin O to the position 1214)

$\theta_n$: the curve angle of the n-th curved portion $\zeta_n$: the rotational angle of the n-th curved portion $\rho_n$: the curvature radius of the n-th curved portion $l_{pna}$: the driving displacement amount of the wire 101-$n$ $l_{pnb}$: the driving displacement amount of the wire 102-$n$ $l_{pnc}$: the driving displacement amount of the wire 103-$n$ The example illustrated in FIG. 1 may use a configuration in which the base unit 110 has therein an actuator (not illustrated) for pushing and pulling the wires 101-2 to 103-2 of the second curved portion 130 and an actuator (not illustrated) for pushing and pulling the wires 101-3 to 103-3 of the third curved portion 140, like the actuators 111 to 113 for pushing and pulling the wires 101-1 to 103-1 of the first curved portion 120 illustrated in FIG. 2.

Figure 3:
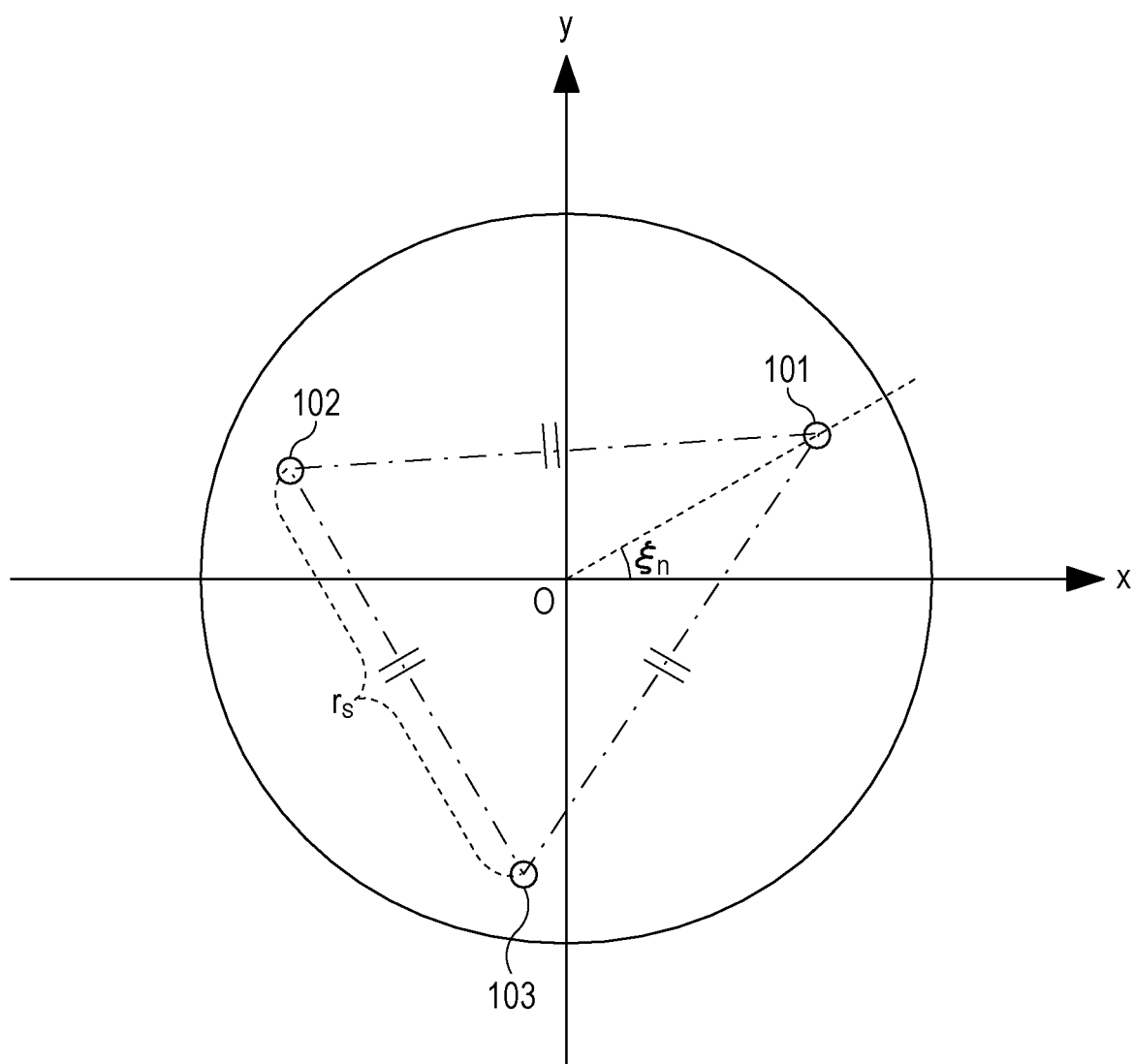
FIG. 3 is a schematic diagram of the first embodiment of the present invention, for defining the arrangement of the wires illustrated in FIG. 2 in an x-y plane.

FIG. 3 is a schematic diagram of the first embodiment of the present invention, for defining the arrangement of the wires 101 to 103 illustrated in FIG. 2 in an x-y plane. In FIG. 3, the wires 101 to 103 are arranged at the vertices of an equilateral triangle with a piece length of $r_s$. A phase angler $\xi_n$ is an angle that determines the arrangement of the wires 101 to 103 of the n-th curved portion. In the present embodiment, $\xi_1=0$.

In the present embodiment, the kinematic model of the continuum robot is derived on the basis of the following assumption.

[1] The wires are deformed at a constant curvature at a curved portion (at individual curved portions if there are multiple curved portions).

[2] The torsional deformation of the wires is not taken into account.

[3] The wires are not deformed in the longitudinal direction.

[4] The friction between the wire guided and the wires is not taken into account.

In this case, the relationship between the driving displacement amount $l_{p1a}$, the driving displacement amount $l_{p1b}$ of the wire 102-1, and the driving displacement amount $l_{p1c}$ of the wire 103-1 of the wire 101-1 of the first curved portion 120 illustrated in FIG. 2 and the curve angle $\theta_1$ and the rotational angle $\zeta_1$ of the first curved portion 120 are respectively expressed as Eq. (1-1), Eq. (1-2), and Eq. (1-3).

[Math. 1]

$$l_{p1a} = \frac{r_s}{\sqrt{3}} \cos\zeta_1 \theta_1 \qquad (1\text{-}1)$$

-continued $$l_{plb} = -\frac{r_s}{\sqrt{3}}\cos(\pi/3 + \zeta_1)\theta_1 \quad (1-2)$$

$$l_{plc} = -\frac{r_s}{\sqrt{3}}\cos(\pi/3 - \zeta_1)\theta_1 \quad (1-3)$$

Next, the relationship between the driving displacement amount $l_{pna}$ of the wire 101-$n$, the driving displacement amount $l_{pnb}$ of the wire 102-$n$, and the driving displacement amount $l_{pnc}$ of the wire 103-$n$ of the n-th curved portion of the continuum robot 100-1 including a plurality of curved portions illustrated in FIG. 1 and the curve angle $\theta_n$ and the rotational angle $\zeta_a$ of the n-th curved portion are expressed as Eq. (2-1), Eq. (2-2), and Eq. (2-3), respectively.

[Math. 2]

$$l_{pna} = \frac{r_s}{\sqrt{3}}\cos(\zeta_n - \xi_n)\theta_n \quad (2-1)$$

$$l_{pnb} = -\frac{r_s}{\sqrt{3}}\cos(\pi/3 + \zeta_n - \xi_n)\theta_n \quad (2-2)$$

$$l_{pnc} = -\frac{r_s}{\sqrt{3}}\cos(\pi/3 - \zeta_n + \xi_n)\theta_n \quad (2-3)$$

[2. Application to Bronchoscope]

Next, an example in which the continuum robot 100-1 illustrated in FIG. 1 is used for a bronchoscope will be described. Here, an imaging apparatus is fixed to the position 160 of the continuum robot 100-1 illustrated in FIG. 1 for use as a bronchoscope for observing the inside of a bronchial tube, which is the insertion-extraction path 20.

A continuum robot control system according to the present embodiment calculates the driving displacement amounts $l_{pna}$, $l_{pnb}$, and $l_{pnc}$ on the basis of image information obtained by the imaging apparatus while moving the continuum robot 100-1 into the inside of the bronchial tubes by moving the base unit 110 and controls the orientation of the continuum robot 100-1.

Figure 4:
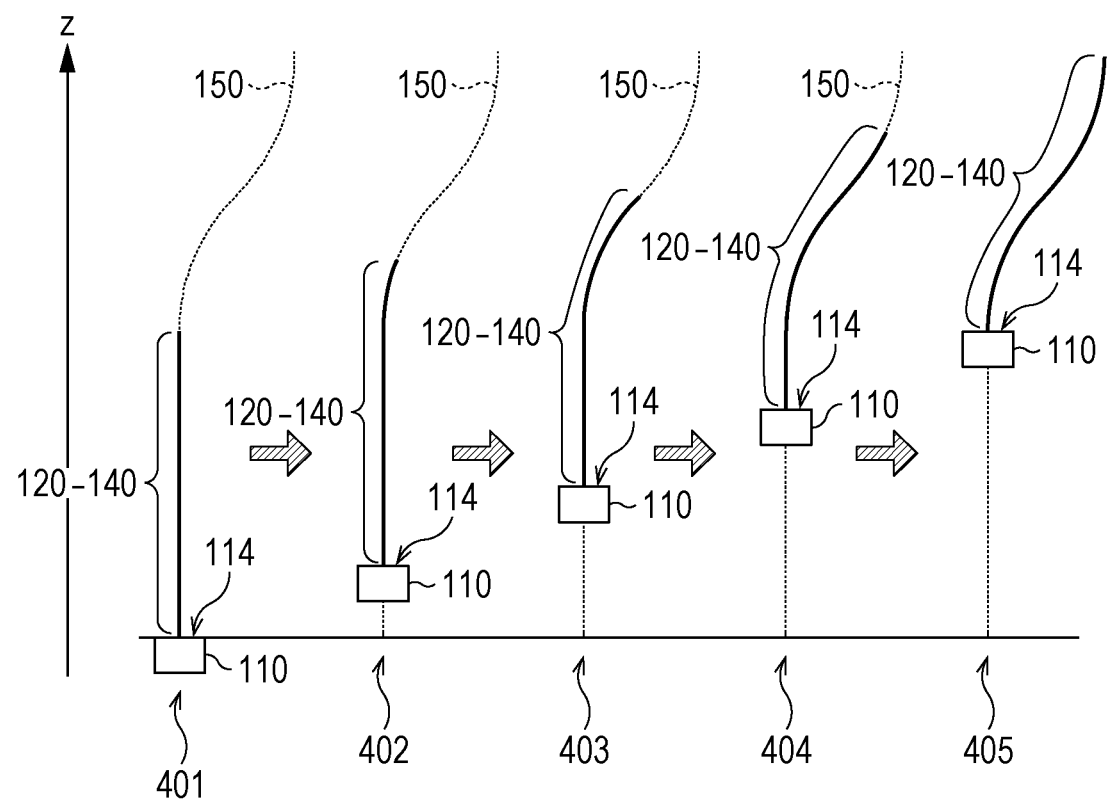
FIG. 4 is a schematic diagram of the first embodiment of the present invention illustrating an example of the progress of the movement of the continuum robot illustrated in FIG. 1.

FIG. 4 is a schematic diagram of the first embodiment of the present invention illustrating an example of the progress of the movement of the continuum robot 100-1 illustrated in FIG. 1. In FIG. 4, the same components as the components illustrated in FIGS. 1 to 3 are given the same reference signs and detailed descriptions will be omitted. FIG. 4 illustrated the z direction (a predetermined direction of the continuum robot 100-1) illustrated in FIGS. 1 and 2. The base unit 110 is disposed on a linear stage extending in the z direction, for example. The manipulator can manually move the continuum robot 100-1 along the linear stage. The linear stage may include an actuator, such as a motor, so as to move the base unit 110 along the linear stage. The linear stage may include a sensor for detecting coordinate information in the z direction (corresponding to a detection apparatus 320 illustrated in FIGS. 5 and 6).

In FIG. 4, time 401 indicates an initial state in which the first curved portion 120 to the third curved portion 140 extending from the upper surface 114 of the base unit 110 in the z direction are not curved. Thereafter, in FIG. 4, the base unit 110 moves in the z direction, and the first curved portion 120 to the third curved portion 140 are curved with the passage of time, from time 402, time 403, time 404, to time 405.

In the following description, for example, the coordinate information in the z direction on the upper surface 114 of the base unit 110 illustrated in FIG. 4 is denoted by $z_b$ in FIG. 1. Since the curve angle $\theta_n$ and the rotational angle $\zeta_n$ of the n-th curved portion depend on the coordinate information $z_b$ indicating the position of the base unit 110, they can be expressed as $\theta_n(z_b)$ and $\zeta_n(z_b)$, respectively. The driving displacement amounts $l_{pna}$, $l_{pnb}$, and $l_{pnc}$ of the wires 101-$n$ to 103-$n$ also depend on the coordinate information $z_b$ and can be expressed as $l_{pna}(z_b)$, $l_{pnb}(z_b)$, and $l_{pnc}(z_b)$, respectively.

Figure 5:
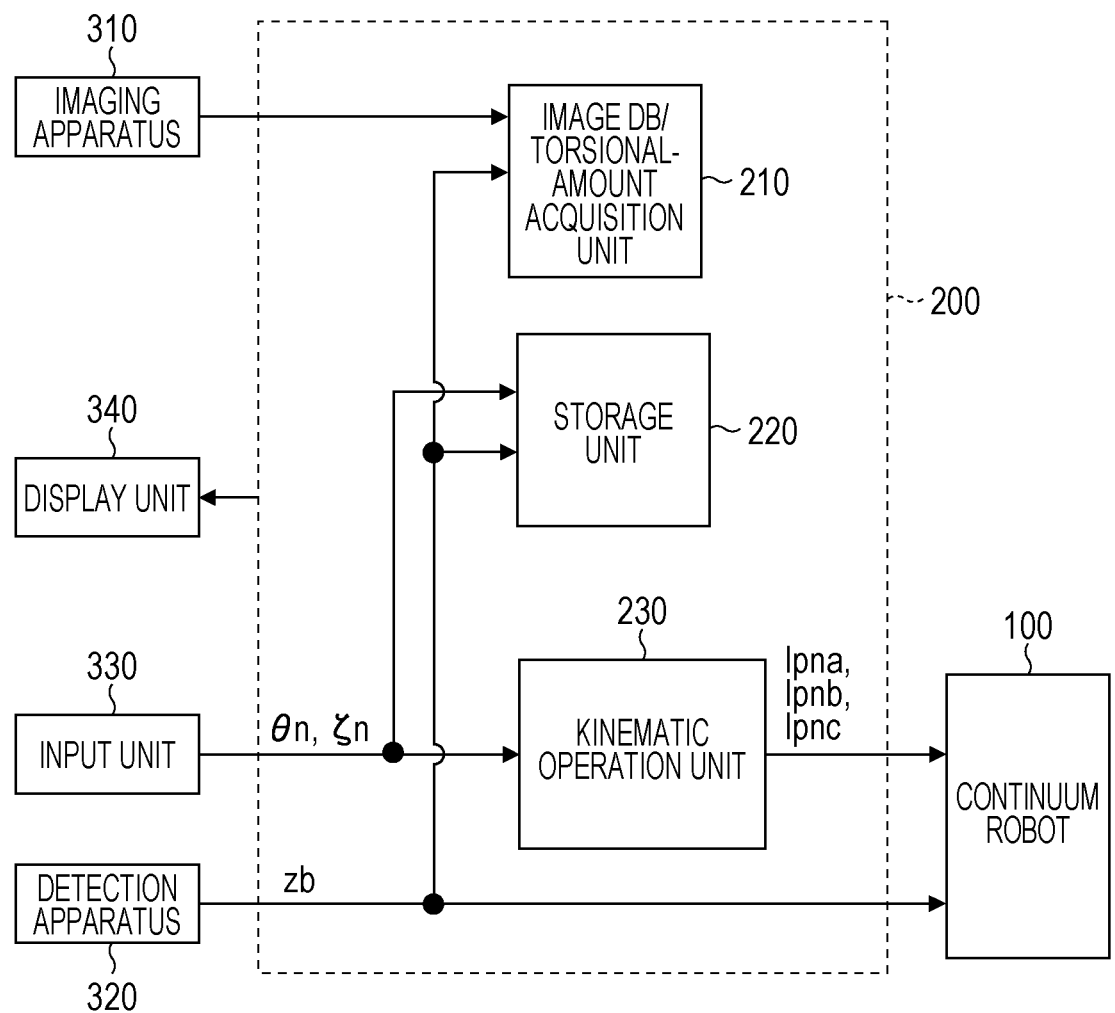
FIG. 5 is a schematic diagram illustrating an example of the functional configuration of a control system for a continuum robot according to the first embodiment of the present invention, illustrating the flow of a signal when the continuum robot is moved in the forward direction.

FIG. 5 is a schematic diagram illustrating an example of the functional configuration of a control system 10-1 for a continuum robot according to the first embodiment of the present invention, illustrating the flow of a signal when the continuum robot 100 is moved in the forward direction.

As illustrated in FIG. 5, the continuum-robot control system 10-1 includes a continuum robot 100, a continuum-robot control apparatus 200, an imaging apparatus 310, a detection apparatus 320, an input unit 330, and a display unit 340.

In the present embodiment, the continuum robot 100 illustrated in FIG. 5 is an application of the continuum robot 100-1 illustrated in FIG. 1. Alternatively, the present invention may employ a continuum robot 100-2 illustrated in FIG. 10.

The continuum-robot control apparatus 200 includes an image DB/torsional-amount acquisition unit 210, a storage unit 220, and a kinematic operation unit 230. The components of the continuum-robot control apparatus 200 will be described later.

In the present embodiment, the imaging apparatus 310 is mounted on the continuum robot 100-1 at the position 160 in FIG. 1 and images an area in the direction of movement of the continuum robot 100-1 to generate image information on the inside of the insertion-extraction path 20, for example.

The detection apparatus 320 detects the coordinate information $z_b$ in the z direction on the upper surface 114 of the base unit 110, as described with reference to FIG. 4, and outputs the detected coordinate information $z_b$ to the continuum-robot control apparatus 200. In the example illustrated in FIG. 4, the detection apparatus 320 detects coordinate information $z_b$ for each of time 401 to time 405 and outputs the coordinate information $z_b$ to the continuum-robot control apparatus 200.

The input unit 330 is a device for the manipulator, such as an operator, to input an operation and includes, for example, a keyboard and a mouse.

The display unit 340 displays a variety of information under the control of the continuum-robot control apparatus 200. For example, the display unit 340 displays image information generated by the imaging apparatus 310, input information input from the input unit 330, coordinate information $z_b$ detected by the detection apparatus, and information obtained by processing performed by the continuum-robot control apparatus 200.

The image DB/torsional-amount acquisition unit 210 includes an image database (image DB) that stores the image information obtained by the imaging apparatus 310 and a torsional-amount acquisition unit that obtains the torsional amount of the continuum robot 100-1 on the basis of the image information. In the example illustrated in FIG. 5, the image DB/torsional-amount acquisition unit 210 obtains the torsional amount of the continuum robot 100-1 on the basis of the image information obtained by the imaging apparatus 310 and the coordinate information $z_b$ on the continuum robot 100-1 in the z direction (a predetermined direction) detected by the detection apparatus 320.

When the continuum robot 100-1 in FIG. 5 is moved in the forward direction, the storage unit 220 stores the image information obtained by the imaging apparatus 310 and stored in the image DB/torsional-amount acquisition unit 210 and the coordinate information $z_b$ detected by the detection apparatus 320 in association with each other. In this case, the storage unit 220 can also store information on the curve angle $\theta_n$ and the rotational angle $\zeta_n$ input from the input unit 330 in association with each other.

The kinematic operation unit 230 performs processing for setting the respective driving displacement amounts $l_{pna}$, $l_{pnb}$, and $l_{pnc}$ of the wires 101 to 103 driven by the actuators 111 to 113 serving as a driving mechanism. The kinematic operation unit 230 controls the driving of the continuum robot 100-1 on the basis of the set driving displacement amounts $l_{pna}$, $l_{pnb}$, and $l_{pnc}$.

For example, when the continuum robot 100-1 is moved forward in the insertion-extraction path 20 illustrated in FIG. 5, the curve angle $\theta_n(z_b)$, the rotational angle $\zeta_n(z_b)$, and the driving displacement amounts $l_{pna}(z_b)$, $l_{pnb}(z_b)$, and $l_{pnc}(z_b)$ at the plurality of positions of the insertion-extraction path 20 are stored in the storage unit 220. At the same time, the image information obtained by the imaging apparatus 310 and the coordinate information $z_b$ detected by the detection apparatus 320 are stored in the image DB/torsional-amount acquisition unit 210 and the storage unit 220 in association with each other.

Figure 6:
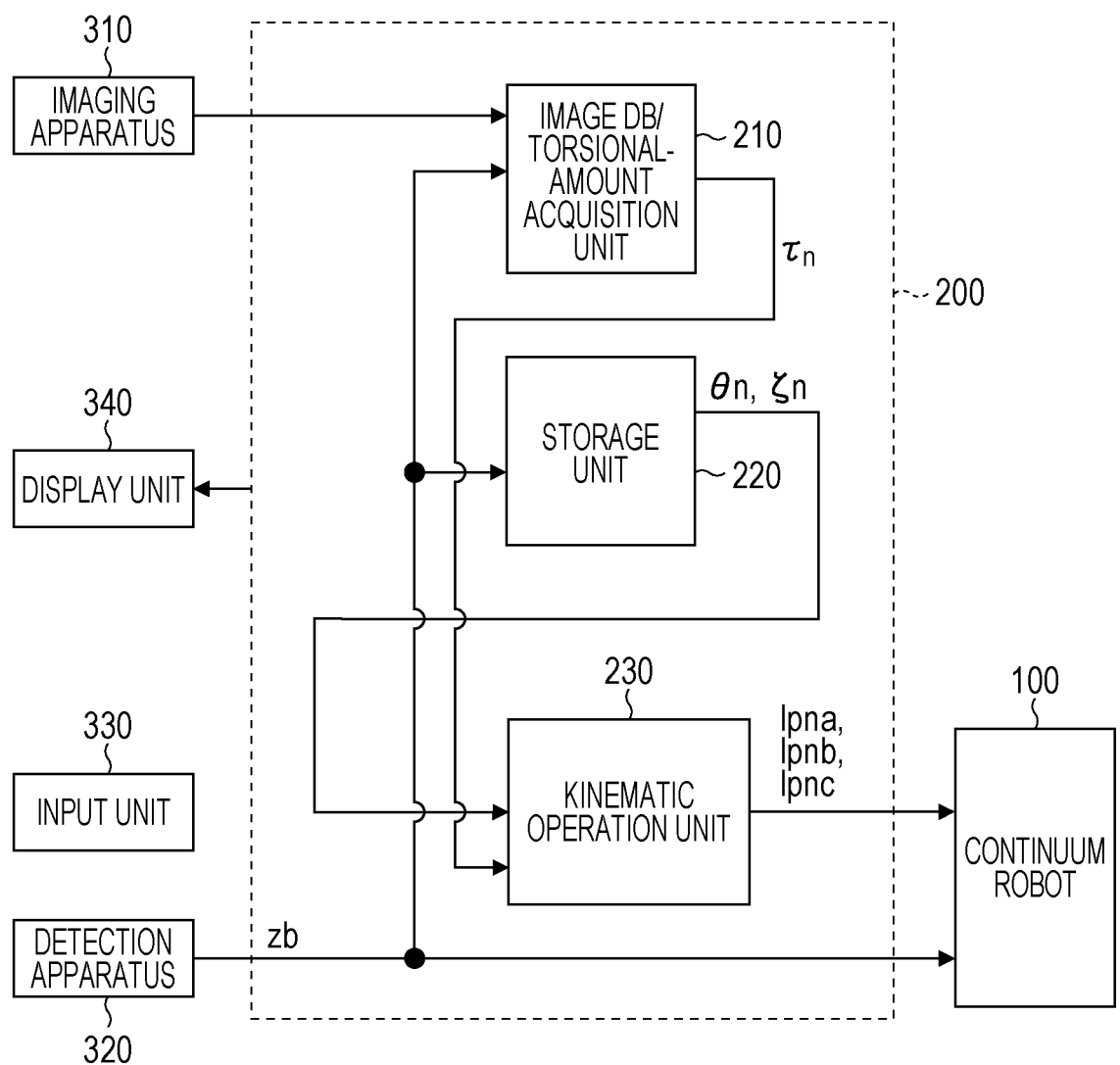
FIG. 6 is a schematic diagram illustrating an example of the functional configuration of the continuum robot control system according to the first embodiment of the present invention, illustrating the flow of a signal when the continuum robot is moved in the rearward direction.

FIG. 6 is a schematic diagram illustrating an example of the functional configuration of the control system 10-1 for a continuum robot according to the first embodiment of the present invention, illustrating the flow of a signal when the continuum robot 100 is moved in the rearward direction. In FIG. 6, the same components as those in FIG. 5 are given the same reference signs.

In the present embodiment, the continuum robot 100 illustrated in FIG. 6 is an application of the continuum robot 100-1 illustrated in FIG. 1, as in FIG. 5 described above. Alternatively, the present invention may employ the continuum robot 100-2 illustrated in FIG. 10.

The imaging apparatus 310 of the present embodiment is configured to image an area in the forward direction of the continuum robot 100-1. F or that reason, when the continuum robot 100-1 is moved in the rearward direction, the imaging apparatus 310 cannot obtain image information on an area in the rearward direction. Therefore, in the present embodiment, the driving displacement amounts $l_{pna}$, $l_{pnb}$, and $l_{pnc}$ are set using information that is stored in the storage unit 220 when the continuum robot 100-1 in FIG. 5 is moved forward, and the driving of the continuum robot 100-1 is controlled.

Also when the continuum robot 100-1 is moved rearward in the insertion-extraction path 20 illustrated in FIG. 6, the image information obtained by the imaging apparatus 310 and the coordinate information $z_b$ detected by the detection apparatus 320 are stored in the image DB/torsional-amount acquisition unit 210 and the storage unit 220 in association with each other.

When the continuum robot 100-1 illustrated in FIG. 6 is moved rearward, the image DB/torsional-amount acquisition unit 210 obtains the torsional amount τ of the continuum robot 100-1 from the amount of rotation of the image using image information at forward movement and rearward movement obtained at the same position (including substantially the same position) of the insertion-extraction path 20 on the basis of the coordinate information $z_b$. In other words, in the case of FIG. 6, the image DB/torsional-amount acquisition unit 210 obtains the torsional amount τ at each position of the insertion-extraction path 20 using, of the image information stored in the storage unit 220, image information stored in association with the coordinate information $z_b$ on each position.

When the continuum robot 100-1 illustrated in FIG. 6 is moved rearward, the kinematic operation unit 230 performs processing for setting the respective driving displacement amounts $l_{pna}$, $l_{pnb}$, and $l_{pnc}$ of the wires 101 to 103 on the basis of the torsional amount τ obtained by the image DB/torsional-amount acquisition unit 210. The kinematic operation unit 230 that performs this processing serves as a setting unit in the present invention. The kinematic operation unit 230 controls the driving of the continuum robot 100-1 on the basis of the set driving displacement amounts $l_{pna}$, $l_{pnb}$, and $l_{pnc}$.

Figure 7:
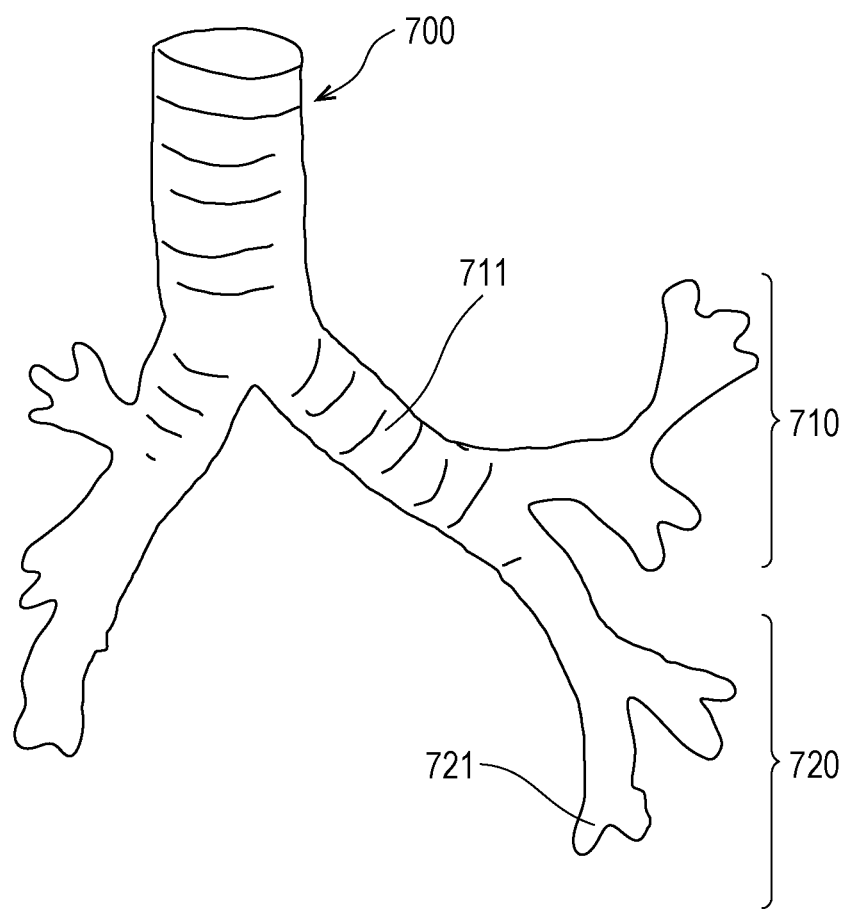
FIG. 7 is a schematic diagram of the first embodiment of the present invention, illustrating an example in which bronchial tubes are used as the insertion-extraction path illustrated in FIG. 1.

FIG. 7 is a schematic diagram of the first embodiment of the present invention, illustrating an example in which bronchial tubes 700 are used as the insertion-extraction path 20 in FIG. 1.

Suppose that the continuum robot 100-1 is moved forward to observe a region of the bronchial tubes 700 to a position 721 of the left lower lobe bronchi 720 using the imaging apparatus 310 and thereafter the continuum robot 100-1 is moved rearward. In this case, the image DB/torsional-amount acquisition unit 210 first obtains image information at individual positions when the imaging apparatus 310 is moved forward to the position 721. Likewise, the image DB/torsional-amount acquisition unit 210 obtains image information at individual positions when the imaging apparatus 310 is moved rearward from the position 721. Then, the image DB/torsional-amount acquisition unit 210 obtains the torsional amount τ of the continuum robot 100-1 from the amount of rotation of the images on the basis of the coordinate information $z_b$ using, for example, image information at forward movement and rearward movement obtained at a position 711 of the left upper lobe bronchi 710 of the bronchial tubes 700. In other words, in the case of FIG. 6, the image DB/torsional-amount acquisition unit 210 obtains the torsional amount τ at individual positions of the insertion-extraction path 20 using, of the image information stored in the storage unit 220, image information stored in association with the coordinate information $z_b$ at the individual positions. Here, an example of the position used in comparing image information obtained during forward movement and during rearward movement is the position 711 at which the divergence of the left upper lobe bronchi 710 and the left lower lobe bronchi 720 of the bronchial tubes 700 can be observed. However, this is not intended to limit the present embodiment.

Figure 8A:
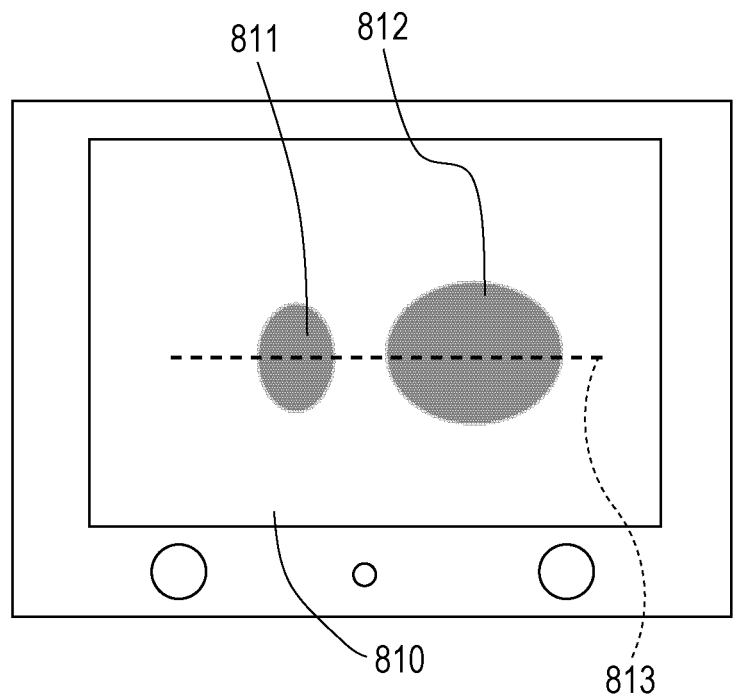
FIG. 8A is a schematic diagram of the first embodiment of the present invention, illustrating an example of image information during forward movement and rearward movement obtained at the position illustrated in FIG. 7.
Figure 8B:
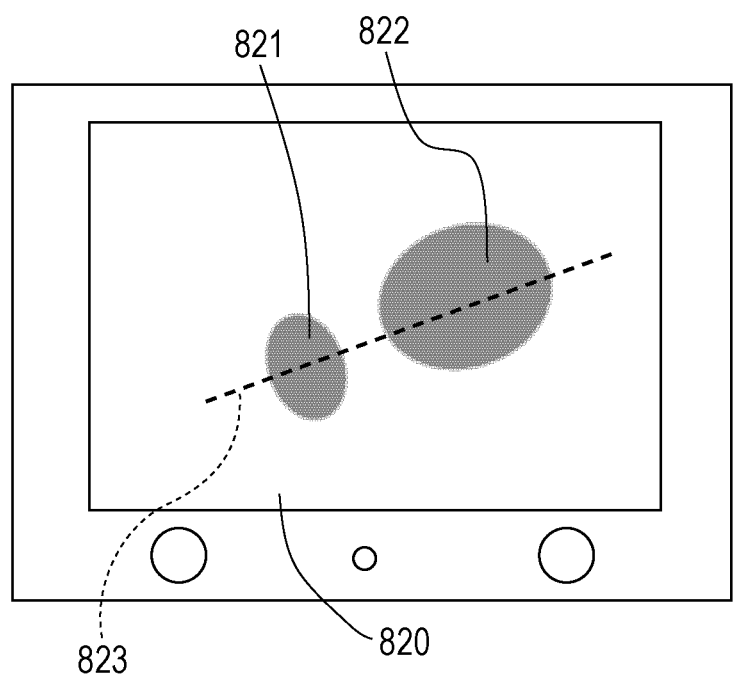
FIG. 8B is a schematic diagram of the first embodiment of the present invention, illustrating an example of image information during forward movement and rearward movement obtained at the position illustrated in FIG. 7.

FIG. 8 is a schematic diagram of the first embodiment of the present invention, illustrating an example of the image information during forward movement and rearward movement obtained at the position 711 illustrated in FIG. 7. Specifically, FIG. 8 illustrates an example of images displayed on the display unit 340 on the basis of the image information obtained during forward movement and rearward movement. More specifically, FIG. 8A illustrates an image 810 during forward movement displayed on the display unit 340 on the basis of image information obtained during forward movement, FIG. 8B illustrates an image 820 obtained during rearward movement displayed on the display unit 340 on the basis of image information obtained during rearward movement.

The image 810 obtained during forward movement illustrated in FIG. 8A includes a path area 811 of the left upper lobe bronchi 710 in FIG. 7 and a path area 812 of the left lower lobe bronchi 720 in FIG. 7. The image 820 obtained during rearward movement illustrated in FIG. 8B includes a path area 821 of the left upper lobe bronchi 710 in FIG. 7 and a path area 822 of the left lower lobe bronchi 720 in FIG. 7. In the present embodiment, the image DB/torsional-amount acquisition unit 210 obtains the torsional amount τ by comparing the image 810 obtained during forward movement illustrated in FIG. 8A and the image 820 obtained during rearward movement illustrated in FIG. 8B. For example, the image DB/torsional-amount acquisition unit 210 obtains the torsional amount τ by extracting the outlines of the path area 811 and the path area 812 from the image 810 obtained during forward movement and the outlines of the path area 821 and the path area 822 from the image 820 obtained during rearward movement and comparing the inclination of a straight line 813 connecting the center of the outlines of the path area 811 and the path area 812 and the inclination of a straight line 823 connecting the center of the outlines of the path area 821 and the path area 822 to each other. In other words, the image DB/torsional-amount acquisition unit 210 obtains the torsional amount τ on the basis of the image information and structural information on the insertion-extraction path 20 into which the continuum robot 100-1 is inserted. In the example illustrated in FIG. 8, the image obtained during rearward movement is twisted at an amount of about 20° with respect to the image obtained during forward movement. In the present embodiment, such comparison of images is performed at a plurality of characteristic positions.

Eq. (2-1), Eq. (2-2), and Eq. (2-3) described above can be rewritten to Eq. (3-1), Eq. (3-2), and Eq. (3-3), respectively, as follows, where $\tau_n$ is the torsional amount τ of the n-th curved portion.

[Math. 3]

$$l_{pna}(z_b) = \frac{r_s}{\sqrt{3}} \cos(\zeta_n - (\xi_n - \tau_n))\theta_n(z_b) \qquad (3-1)$$

$$l_{pnb}(z_b) = -\frac{r_s}{\sqrt{3}} \cos(\pi/3 + \zeta_n - (\xi_n - \tau_n))\theta_n(z_b) \qquad (3-2)$$

$$l_{pnc}(z_b) = -\frac{r_s}{\sqrt{3}} \cos(\pi/3 - \zeta_n + (\xi_n - \tau_n))\theta_n(z_b) \qquad (3-3)$$

In the present embodiment, the kinematic operation unit 230 sets the driving displacement amounts $l_{pna}(z_b)$, $l_{pnb}(z_b)$, and $l_{pnc}(z_b)$ given by Eq. (3-1), Eq. (3-2), and Eq. (3-3), for example. Specifically, the kinematic operation unit 230 sets the driving displacement amounts described above on the basis of the torsional amount $\tau_n$, the curve angle $\theta_n$, and the rotational angle $\zeta_n$. The kinematic operation unit 230 controls the driving of the continuum robot 100-1 using the set driving displacement amounts.

The torsional amount $\tau_e$ can be obtained from the images during forward movement and during rearward movement captured by the imaging apparatus 310. The torsional amount $\tau_n$ may be constant in all the curved portions and may be expressed as Eq. (4), where e is the number of curved portions.

[Math. 4]

$$\tau_n = \tau_e \qquad (4)$$

The torsional amount $\tau_n$ may change continuously as expressed as Eq. (5) using the length of each curved portion, $l_n$, and the entire length of the curved portions,

[Math. 5]

$$L\left(=\sum_{n=1}^{e} l_n\right), \qquad (5)$$

$$\tau_n = \tau_e \frac{\sum_{k=1}^{n} l_k}{L}$$

The torsional amount $\tau_n$ of each curved portion may be multiplied by an appropriate correction coefficient.

If it is difficult to compare the images obtained during forward movement and during rearward movement because of body motion due to breathing, monitoring the breathing and comparing only images captured at a specific timing of the breathing allows increasing the estimation accuracy of the rotation amount of the images. This can be achieved, for example, by the imaging apparatus 310 obtaining moving images at individual positions and by the image DB/torsional-amount acquisition unit 210 comparing images with the same degree of deformation of the lumen (insertion-extraction path 20) due to breathing during forward movement and during rearward movement.

In the above configuration, the curve angle $\theta_n$ and the rotational angle $\zeta_n$ of the continuum robot 100-1 are controlled by displacing all of the three wires 101 to 103. However, this is not intended to limit the present invention. For example, a configuration in which the curve angle $\theta_n$ and the rotational angle $\zeta_n$ of the continuum robot 100-1 are controlled by fixing one of the three wires 101 to 103 and displacing the other two wires can provide the same advantageous effects and can be employed in the present invention. In this configuration, if the displacement of the wire 101 is fixed so that the wire 101 is a fixed-length wire, the kinematic operation unit 230 can set the driving displacement amounts $l_{pna}$, $l_{pnb}$, and $l_{pnc}$ expressed as Eq. (6-1), Eq. (6-2), and Eq. (6-3), respectively.

[Math. 6]

$$l_{pna}=0 \qquad (6-1)$$

$$l_{pnb}=\cos(\pi/6+\zeta_n-\xi_n)r_s\theta_n \qquad (6-2)$$

$$l_{pnc}=\cos(\pi/6-\zeta_n+\xi_n)r_s\theta_n \qquad (6-3)$$

The kinematic operation unit 230 can also set driving displacement amounts $l_{pna}$, $l_{pnb}$, and $l_{pnc}$ after the torsional amount $\tau_n$ is obtained, as in Eq. (7-1), Eq. (7-2), Eq. (7-3), respectively.

[Math. 7]

$$l_{pna}=0 \qquad (7-1)$$

$$l_{pnb}=\cos(\pi/6+\zeta_n-(\xi_n-\tau_n))r_s\theta_n \qquad (7-2)$$

$$l_{pnc}=\cos(\pi/6-\zeta_n+(\xi_n-\tau_n))r_s\theta_n \qquad (7-3)$$

In the continuum-robot control apparatus 200 according to the first embodiment, the image DB/torsional-amount acquisition unit 210 obtains the torsional amount τ of the continuum robot 100-1, and the kinematic operation unit 230 sets the driving displacement amounts of the wires on the basis of the torsional amount.

This configuration allows suppressing a decrease in the accuracy of drive control of the continuum robot even if the continuum robot is twisted. This allows the continuum robot to be smoothly moved rearward even if the continuum robot has no rearward view. Furthermore, the driving displacement amounts of the wires can be corrected according to the torsional amount. This allows the continuum robot to be controlled to a desired orientation even if the continuum robot is twisted.

Second Embodiment

Next, a second embodiment of the present invention will be described. In the second embodiment described below, descriptions of elements common to those of the first embodiment will be omitted, and differences from the first embodiment will be described.

In the second embodiment, the continuum robot 100 is used not only for observing the inside of bronchial tubes but also as a guide sheath through which a biopsy tool, such as forceps and a suction needle, is passed.

Figure 9:
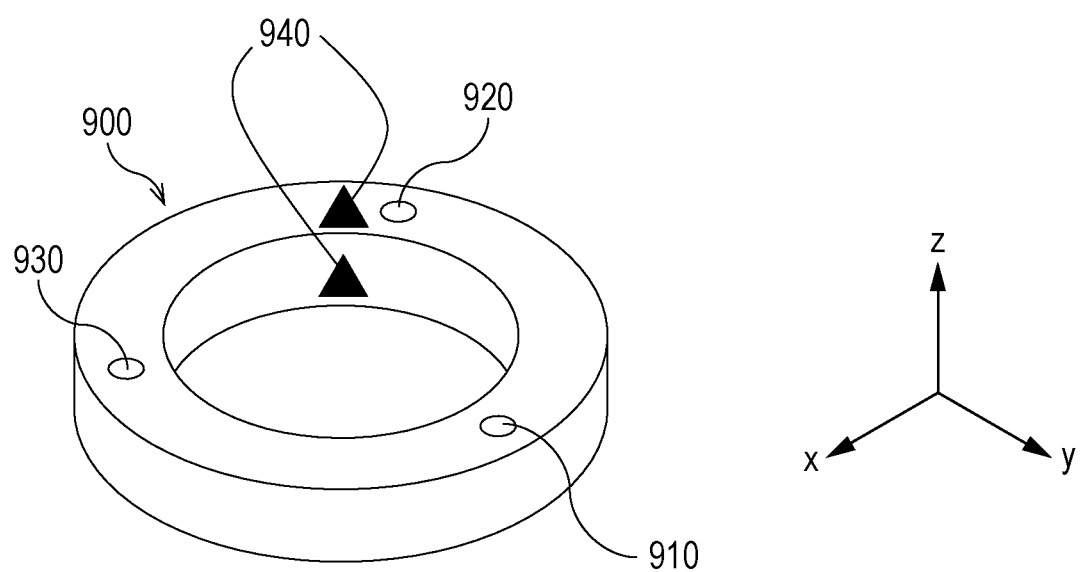
FIG. 9 is a schematic diagram illustrating an example of one wire guide of a continuum robot according to a second embodiment of the present invention.

FIG. 9 is a schematic diagram illustrating an example of one wire guide 900 of the continuum robot 100 according to the second embodiment of the present invention. FIG. 9 illustrates the x-axis, the y-axis, and the z-axis, as in FIG. 1.

The wire guide 900 has a doughnut shape, as illustrated in FIG. 9. As illustrated in FIG. 9, the wire guide 900 has a through-hole 910 in which the wire 101 is fixed, a through-hole 920 in which the wire 102 is passed or fixed, a through-hole 930 in which the wire 103 is passed or fixed, and marks 940.

Figure 10:
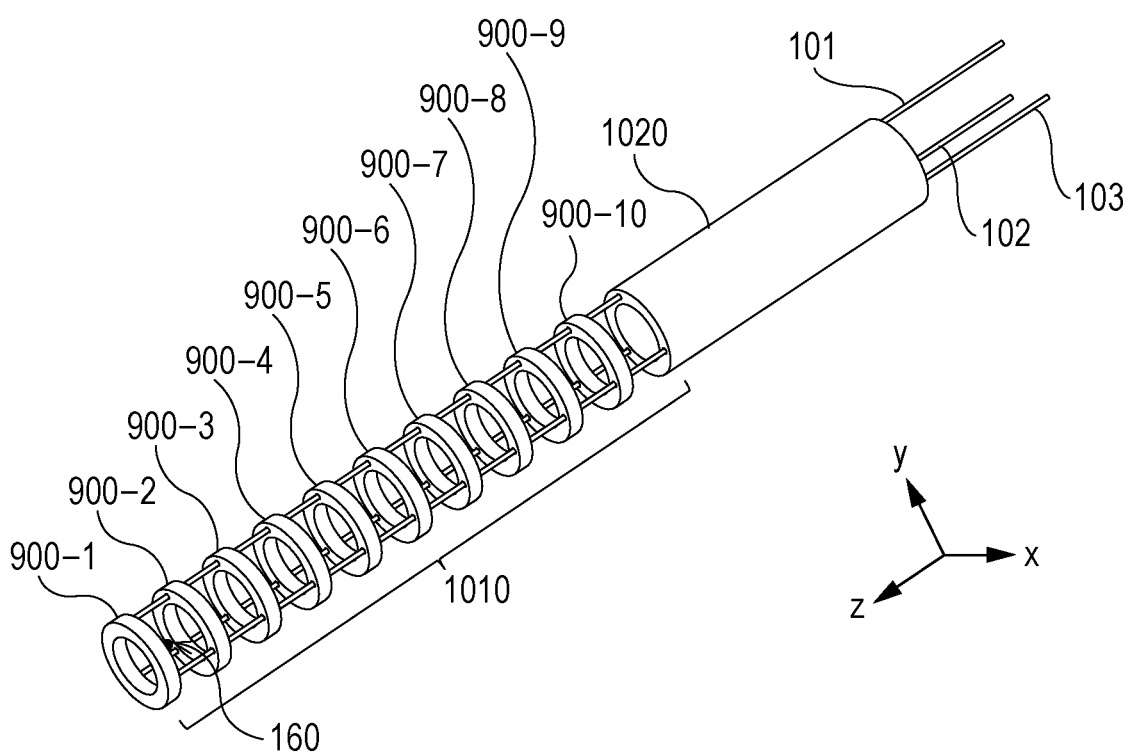
FIG. 10 is a diagram illustrating, in outline, an example of the configuration of the continuum robot according to the second embodiment of the present invention.

FIG. 10 is a diagram illustrating, in outline, an example of the configuration of a continuum robot 100-2 according to the second embodiment of the present invention. FIG. 10 illustrates the x-axis, the y-axis, and the z-axis, as in FIG. 1.

As illustrated in FIG. 10, the continuum robot 100-2 includes a curved portion 1010 and a sleeve 1020 disposed between the curved portion 1010 and a base unit (not illustrated, for example the base unit 110 illustrated in FIG. 2).

The curved portion 1010 includes the wire guide 900 illustrated in FIG. 9 at multiple (ten) positions in the z direction. Specifically, the curved portion 1010 includes wire guides 900-1 to 900-10. The continuum robot 100-2 illustrated in FIG. 10 may be equipped with the imaging apparatus 310 at the position 160. The position 160 at which the imaging apparatus 310 is disposed may not be between the wire guide 900-1 and the wire guide 900-10. The imaging apparatus 310 disposed at the position 160 images an area in the forward direction of the continuum robot 100-2 (z direction) to generate image information. In the wire guide 900-1, the wires 101, 102, and 103 are fixed in the through-holes 910, 920, and 930, respectively. In the wire guides 900-2 to 900-10, the wire 101 is fixed in the through-hole 910, and the other through-holes 920 and 930 allow the wires 102 and 103 to pass through.

The sleeve 1020 allows the wires 101 to 103 to pass through without fixing them.

The continuum robot 100-2 illustrated in FIG. 10 allows a biopsy tool to pass through. When moving (forward) toward a tumor (the target of biopsy), the continuum robot 100-2 moves forward while observing an area in front of the continuum robot 100-2 in the insertion-extraction path 20 using the imaging apparatus (a fiber scope camera) 310 disposed in the wire guide.

In the present embodiment, the continuum robot 100-2 is moved forward, and at the point in time where it reaches the tumor for biopsy, the manipulator, such as an operator, extracts the imaging apparatus 310 from the continuum robot 100-2 and inserts the biopsy tool into the continuum robot 100-2. After obtaining a sample with the biopsy tool, the manipulator extracts the biopsy tool, inserts and disposes the imaging apparatus 310 into the continuum robot 100-2 again, and moves the continuum robot 100-2 rearward. Thus, when the continuum robot 100-2 is used as a guide sheath through which the biopsy tool is passed, the imaging apparatus 310 is not fixed in the continuum robot 100-2.

When inserting the imaging apparatus (fiberscope camera) 310, the manipulator, such as an operator, determines the position of the imaging apparatus 310 in the z direction so that the marks 940 of the wire guide 900-1 at the most distal end of the continuum robot 100-2 always fall within the imagable range of the imaging apparatus 310. In other words, in the present embodiment, the imaging apparatus 310 has a configuration for imaging an area including the marks 940 of the wire guide 900-1.

While the marks 940 are at the same positions when an image obtained by the imaging apparatus 310 is displayed on the display unit 340, the positional relationship between the imaging apparatus (fiberscope camera) 310 and the continuum robot 100-2 is kept. For example, when the positions of the marks 940 rotate in the image, the amount of rotation β corresponds to the amount of rotation of the imaging apparatus (fiberscope camera) 310 in the continuum robot 100-2.

In comparison between images obtained during forward movement and during rearward movement of the continuum robot 100-2, the factors of rotation of the positions of the marks 940 may be the twist of the continuum robot 100-2 itself and the rotation of the imaging apparatus 310 in the continuum robot 100-2. The torsional amount $\tau_e$ of the continuum robot 100-2 itself at the most distal end is expressed as Eq. (8), where α is the rotation amount of the images during forward movement and rearward movement, and β is the rotation amount. In the present embodiment, the image DB/torsional-amount acquisition unit 210 employs a configuration in which the torsional amount $\tau_e$ is obtained on the basis of the positions of the marks 940 contained in the image information.

[Math. 8]

$$\tau_e = \alpha - \beta \qquad (8)$$

Applying Eq. (8) to Eq. (4) or Eq. (5) and substituting it into Eq. (3-1) to Eq. (3-3) allows setting the driving displacement amounts of the wires that take into account both of the torsional amount of the continuum robot 100-2 and the amount of rotation of the imaging apparatus 310 in the continuum robot 100-2. In the present embodiment, the kinematic operation unit 230 adopts a configuration in which the driving displacement amounts of the wires 101 to 103 are set on the basis of the torsional amount $\tau_e$ obtained by the image DB/torsional-amount acquisition unit 210.

This is a method of correction in the case where the imaging apparatus (fiberscope camera) 310 rotates in the continuum robot 100-2. The smaller the amount of rotation, the better. For example, a configuration in which magnets are attached to part of the wire guide 900 and the imaging apparatus 310 to prevent the rotation is also applicable. Another configuration in which the wire guide 900 has a groove, and the imaging apparatus 310 has a protrusion, and they are joined together to prevent the rotation is also applicable.

The second embodiment can suppress a decrease in the accuracy of drive control of the continuum robot even if the continuum robot is twisted, as in the first embodiment described above.

Third Embodiment

Next, a third embodiment of the present invention will be described. In the third embodiment described below, descriptions of elements common to those of the first and second embodiments will be omitted, and differences from the first and second embodiments will be described.

In the third embodiment, simplification of re-examination will be described.

When a patient undergoes a bronchoscopic examination using the continuum robot 100 (for example, the continuum robot 100-1 illustrated in FIG. 1), $\theta_n(z_b)$, $\zeta_n(z_b)$, $l_{pna}(z_b)$, $l_{pnb}(z_b)$, and $l_{pnc}(z_b)$ during forward movement and rearward movement to the target site and the coordinate information $z_b$ are stored in the image DB/torsional-amount acquisition unit 210 and the storage unit 220 illustrated in FIG. 6.

At the second examination of the same patient, the continuum robot 100 (base unit 110) is moved forward and rearward, using $l_{pna}(z_b)$, $l_{pnb}(z_b)$, and $l_{pnc}(z_b)$ at the first examination as the driving displacement amounts of the wires of the continuum robot 100 for the forward movement and rearward movement. The flow of the signal at that time with the functional configuration of the continuum robot control system 10 is illustrated in FIG. 6 described above.

In the third embodiment, the image DB/torsional-amount acquisition unit 210 illustrated in FIG. 6 compares an image at the first examination and an image at the second examination for each of forward movement and rearward movement to obtain the torsional amount of the continuum robot 100 from the amount of rotation of the images.

If the torsional amount obtained by the image DB/torsional-amount acquisition unit 210 is equal to or less than a threshold, the continuum-robot control apparatus 200 can use a configuration in which the continuum robot 100 is controlled using the same driving displacement amounts of the wires 101 to 103 as the amounts obtained at the first examination. This allows the manipulator, such as an operator, to easily move the continuum robot 100 to the target site.

In contrast, if the torsional amount obtained by the image DB/torsional-amount acquisition unit 210 exceeds the threshold, the continuum-robot control apparatus 200 can use a configuration in which the continuum-robot control apparatus 200 determines that the continuum robot 100 is twisted, and the torsional amount $\tau_n$ is transmitted from the image DB/torsional-amount acquisition unit 210 to the kinematic operation unit 230. The kinematic operation unit 230 updates the driving displacement amounts of the wires 101 to 103 according to Eq. (3-1) to Eq. (3-2). Using the updated driving displacement amounts of the wires 101 to 103 allows finding all of the driving displacement amounts of the wires 101 to 103 to the target site. This allows the manipulator, such as an operator, to move the continuum robot 100 to the target site even if the continuum robot 100 is twisted.

The threshold of the torsional amount described above is determined from the amount of rotation of the images caused by, for example, a body motion due to breathing. In this case, a plurality of images are obtained at different breathing timings, with the base unit 110 at rest, and the amount of rotation of the images generated at that time is used as the threshold of the torsional amount.

In the above example, the driving displacement amounts of the wires 101 to 103 are updated on the basis of the torsional amount that the image DB/torsional-amount acquisition unit 210 illustrated in FIG. 6 obtains from the image information obtained by the imaging apparatus 310. Alternatively, the manipulator may make fine adjustments to the torsional amount via the input unit 330. For example, a torsional amount input dial, which is one component of the input unit 330, may be disposed at hand of the manipulator, such as an operator, and the manipulator may adjust the torsional amount via the input dial.

The third embodiment can suppress a decrease in the accuracy of drive control of the continuum robot even if the continuum robot is twisted, as in the first embodiment described above.

Fourth Embodiment

Next, a fourth embodiment of the present invention will be described. In the fourth embodiment described below, descriptions of elements common to those of the first to third embodiments will be omitted, and differences from the first to third embodiments will be described.

In the first to third embodiments described above, image information obtained by imaging the inside of the bronchial tubes of the patient using a bronchoscope as the continuum robot 100 are compared. However, the present invention is not limited to the above configuration. The fourth embodiment illustrates a configuration in which another image information on the bronchial tubes generated using another modality and image information generated by the imaging apparatus 310 disposed at a bronchoscope are compared.

Figure 11:
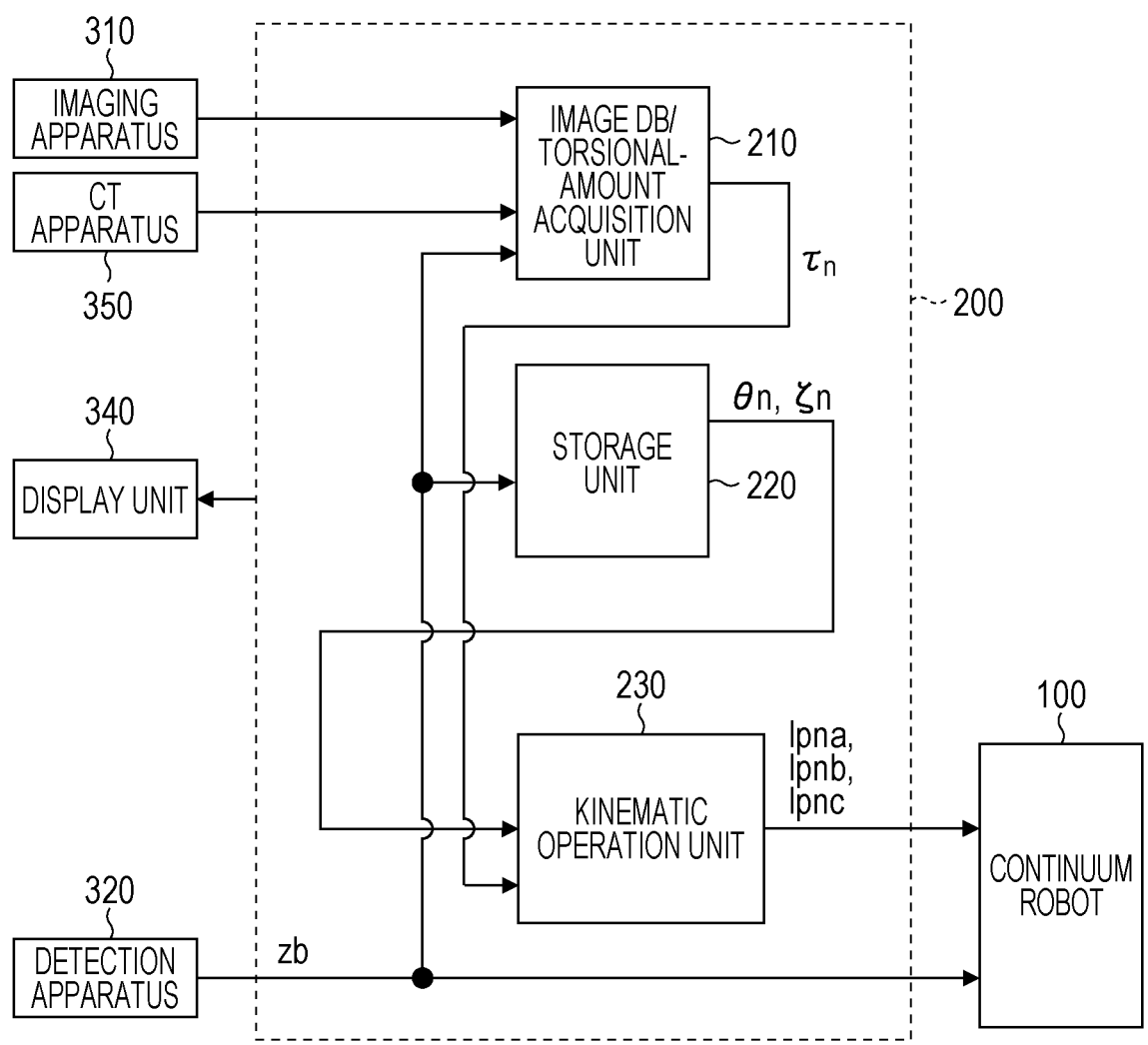
FIG. 11 is a schematic diagram illustrating an example of the functional configuration of a continuum robot control system 10-2 according to a fourth embodiment of the present invention.

FIG. 11 is a schematic diagram illustrating an example of the functional configuration of a continuum robot control system 10-2 according to the fourth embodiment of the present invention. In FIG. 11, the same components as those in FIGS. 5 and 6 are denoted by the same reference signs.

The continuum robot control system 10-2 includes a computed tomography (CT) apparatus 350, in addition to the components of the continuum robot control system 10-1 illustrated in FIGS. 5 and 6.

The CT apparatus 350 is another imaging apparatus different from the imaging apparatus 310 and generates CT-image information which is another image information different from image information obtained by the imaging apparatus 310.

In the present embodiment, the image DB/torsional-amount acquisition unit 210 obtains computed tomography (CT)image information on, for example, the chest of the patient, from the CT apparatus 350 before the bronchoscope is inserted. The image DB/torsional-amount acquisition unit 210 creates a virtual image that is assumed when the bronchoscope is inserted to observe the inside of the bronchial tubes from the obtained CT-image information. The continuum-robot control apparatus 200 virtually moves the base unit 110 forward in the CT image and calculates $\theta_n(z_b)$, $\zeta_n(z_b)$, $l_{pna}(z_b)$, $l_{pnb}(z_b)$, and $l_{pnc}(z_b)$ for a virtual path to the target site. These calculated values and the virtual image information at a characteristic site are stored in the image DB/torsional-amount acquisition unit 210 and the storage unit 220 illustrated in FIG. 11.

When a bronchoscope related to the continuum robot 100 is inserted into a patient, the continuum-robot control apparatus 200 controls the continuum robot 100 using the virtually obtained $l_{pna}(z_b)$, $l_{pnb}(z_b)$, and $l_{pnc}(z_b)$ as the driving displacement amounts of the wires 101 to 103. The image DB/torsional-amount acquisition unit 210 obtains image information generated by the imaging apparatus 310 while the continuum robot 100 is moved forward and compares the feature points between the image information and the virtual image information created from the CT-image information to obtain the torsional amount $\tau_n$ of the continuum robot 100.

When the rotation of the images is detected, the continuum-robot control apparatus 200 determines that the continuum robot 100 is twisted. In this case, the kinematic operation unit 230 sets (corrects) the driving displacement amounts of the wires 101 to 103 according to Eq. (3-1) to Eq. (3-3) on the basis of the torsional amount $\tau_n$ obtained by the image DB/torsional-amount acquisition unit 210.

Although the fourth embodiment illustrates an example in which a bronchoscope is used as the continuum robot 100, the present invention is not limited to the medical field. For example, when the continuum robot 100 of the present invention is used to check pipes, the virtual image information may be created from a computer-aided design (CAD) drawing at piping designing.

The fourth embodiment can suppress a decrease in the accuracy of drive control of the continuum robot even if the continuum robot is twisted, as in the first embodiment described above.

The present invention allows suppressing a decrease in the accuracy of drive control of the continuum robot even if the continuum robot is twisted.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or m ore circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. A control apparatus for a continuum robot including a curved portion that is curved by driving a wire using a driving mechanism, the apparatus comprising:
   a processor that operates to:
   obtain a torsional amount of the continuum robot; and
   set a driving displacement amount of the wire driven by the driving mechanism based on the obtained torsional amount,
   wherein the curved portion includes:
   a plurality of wires extending through a reference plane;
   a first wire guide in which two or more wires of the plurality of wires are fixed at different positions, the first wire guide operating to guide the plurality of wires; and
   a second wire guide provided between the reference plane and the first wire guide, in which a predetermined wire of the plurality of wires is fixed, and which guides the plurality of wires, and
   the driving mechanism drives at least part of the plurality of wires.

2. The control apparatus for a continuum robot according to claim 1, wherein the processor further operates to obtain the torsional amount based on image information obtained by an imaging apparatus mounted to the continuum robot.

3. The control apparatus for a continuum robot according to claim 2, wherein the processor further operates to obtain the torsional amount based on the image information and structural information on a path into which the continuum robot is inserted.

4. The control apparatus for a continuum robot according to claim 2, wherein
   the continuum robot has a mark,
   the imaging apparatus images an area including the mark, and
   the processor further operates to obtain the torsional amount based on a position of the mark contained in the image information.

5. The control apparatus for a continuum robot according to claim 2, wherein the processor further operates to obtain the torsional amount based on the image information obtained by the imaging apparatus and another image information obtained by another imaging apparatus different from the imaging apparatus.

6. The control apparatus for a continuum robot according to claim 2, further comprising a storage medium that stores the image information and coordinate information on the continuum robot in a predetermined direction in association with each other, the coordinate information being detected by a detection apparatus.

7. The control apparatus for a continuum robot according to claim 6, wherein, in a case where the continuum robot moves forward in a path into which the continuum robot is inserted, the storage medium stores the image information and the coordinate information in association with each other at a plurality of positions of the path.

8. The control apparatus for a continuum robot according to claim 7, wherein, in a case where the continuum robot moves rearward in the path, the processor further operates to obtain the torsional amount at individual positions of the path using, of the image information stored in the storage medium, image information stored in association with coordinate information on the individual positions of the path.

9. The control apparatus for a continuum robot according to claim 1, characterized in that the processor further operates to set the driving displacement amount based on the torsional amount and a curve angle and a rotational angle of the curved portion.

10. A method for controlling a continuum robot including a curved portion that is curved by driving a wire using a driving mechanism, the method comprising:

obtaining a torsional amount of the continuum robot; and
setting a driving displacement amount of the wire driven by the driving mechanism based on the torsional amount obtained in the obtaining,
wherein the curved portion includes:
a plurality of wires extending through a reference plane;
a first wire guide in which two or more wires of the plurality of wires are fixed at different positions, the first wire guide operating to guide the plurality of wires; and
a second wire guide provided between the reference plane and the first wire guide, in which a predetermined wire of the plurality of wires is fixed, and which guides the plurality of wires, and
the driving mechanism drives at least part of the plurality of wires.

11. The method for controlling a continuum robot according to claim 10, wherein in the obtaining, the torsional amount is obtained based on image information obtained by an imaging apparatus mounted to the continuum robot.

12. The method for controlling a continuum robot according to claim 11, wherein in the obtaining, the torsional amount is obtained based on the image information and structural information on a path into which the continuum robot is inserted.

13. The method for controlling a continuum robot according to claim 11, wherein
the continuum robot has a mark,
the imaging apparatus images an area including the mark, and
in the obtaining, the torsional amount is obtained based on a position of the mark contained in the image information.

14. The method for controlling a continuum robot according to claim 11, wherein in the obtaining, the torsional amount is obtained based on the image information obtained by the imaging apparatus and another image information obtained by another imaging apparatus different from the imaging apparatus.

15. The method for controlling a continuum robot according to claim 11, further comprising storing the image information and coordinate information on the continuum robot in a predetermined direction in a storage medium in association with each other, the coordinate information being detected by a detection apparatus.

16. The method for controlling a continuum robot according to claim 15, wherein, in a case where the continuum robot moves forward in a path into which the continuum robot is inserted, in the storing, the image information and the coordinate information are stored in association with each other at a plurality of positions of the path.

17. The method for controlling a continuum robot according to claim 16, wherein, in a case where the continuum robot moves rearward in the path, in the obtaining, the torsional amount is obtained at individual positions of the path using, of the image information stored in the storage medium, image information stored in association with coordinate information on the individual positions of the path.

18. The method for controlling a continuum robot according to claim 10, wherein in the setting, the driving displacement amount is set based on the torsional amount and a curve angle and a rotational angle of the curved portion.

19. A non-transitory computer-readable storage medium storing a program for causing a computer to execute a method for controlling a continuum robot including a curved portion that is curved by driving a wire using a driving mechanism, the method comprising:
obtaining a torsional amount of the continuum robot; and
setting a driving displacement amount of the wire driven by the driving mechanism based on the torsional amount obtained in the obtaining,
wherein the curved portion includes:
a plurality of wires extending through a reference plane;
a first wire guide in which two or more wires of the plurality of wires are fixed at different positions, the first wire guide operating to guide the plurality of wires; and
a second wire guide provided between the reference plane and the first wire guide, in which a predetermined wire of the plurality of wires is fixed, and which guides the plurality of wires, and
the driving mechanism drives at least part of the plurality of wires.

* * * * *